United States Patent [19]

Stupay

[11] 4,200,348

[45] Apr. 29, 1980

[54] MEDICAL CLIP

[75] Inventor: Lawrence J. Stupay, Endicott, N.Y.

[73] Assignee: Bunker Ramo Corporation, Oak Brook, Ill.

[21] Appl. No.: 711,455

[22] Filed: Aug. 4, 1976

[51] Int. Cl.² ............................................. H01R 11/22
[52] U.S. Cl. .................................... 339/61 R; 339/261
[58] Field of Search ........... 339/61 R, 108 TP, 200 P, 339/228, 255 P, 260, 261; 128/2.1 E

[56] References Cited

U.S. PATENT DOCUMENTS

| 909,481 | 1/1909 | Tregoning | 339/261 |
|---|---|---|---|
| 3,740,703 | 6/1973 | Sessions | 339/261 |
| 3,774,143 | 11/1973 | Lopin | 339/61 R |

FOREIGN PATENT DOCUMENTS 292340 6/1928 United Kingdom ..................... 339/261

Primary Examiner—Neil Abrams
Attorney, Agent, or Firm—Hill, Van Santen, Steadman, Chiara & Simpson

[57] ABSTRACT

A medical clip, particularly for connecting a lead conductor to an electrode conventionally secured to the skin surface of an animal or human, and which electrode typically comprises a male projection of the button-type; the clip being of a generally V or wishbone configuration, the arms of which carry resilient wire loops normally biased out of overlapping condition but movable upon the application of external force into an overlapped condition wherein the clip may be applied over said button onto said electrode. The clip is provided with means preventing accidental contact with the male electrode when the clip is in position thereon, and with means preventing undesired tilting of the clip thereby minimizing inadvertent and unintentional disassembly of the clip from the electrode.

4 Claims, 7 Drawing Figures

U.S. Patent  Apr. 29, 1980  4,200,348
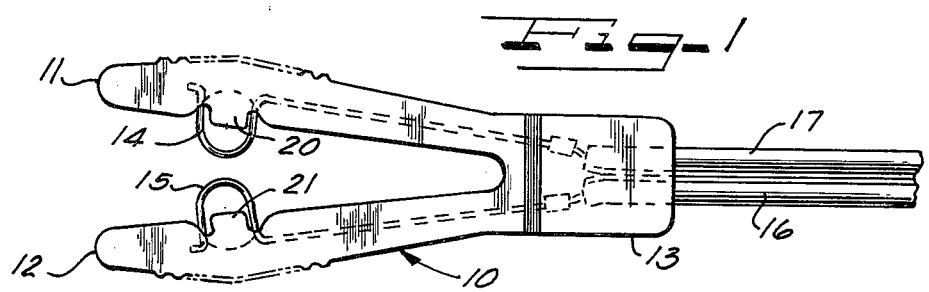
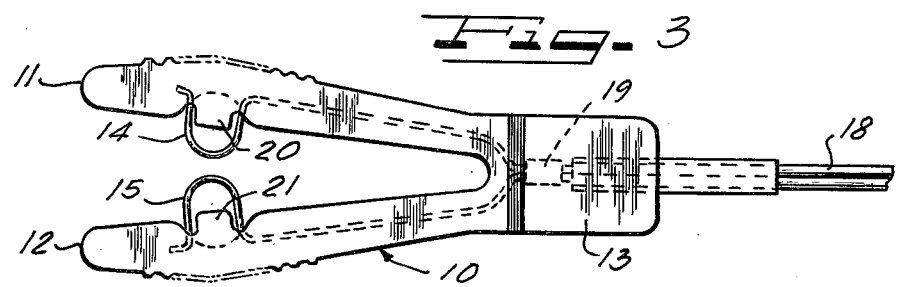
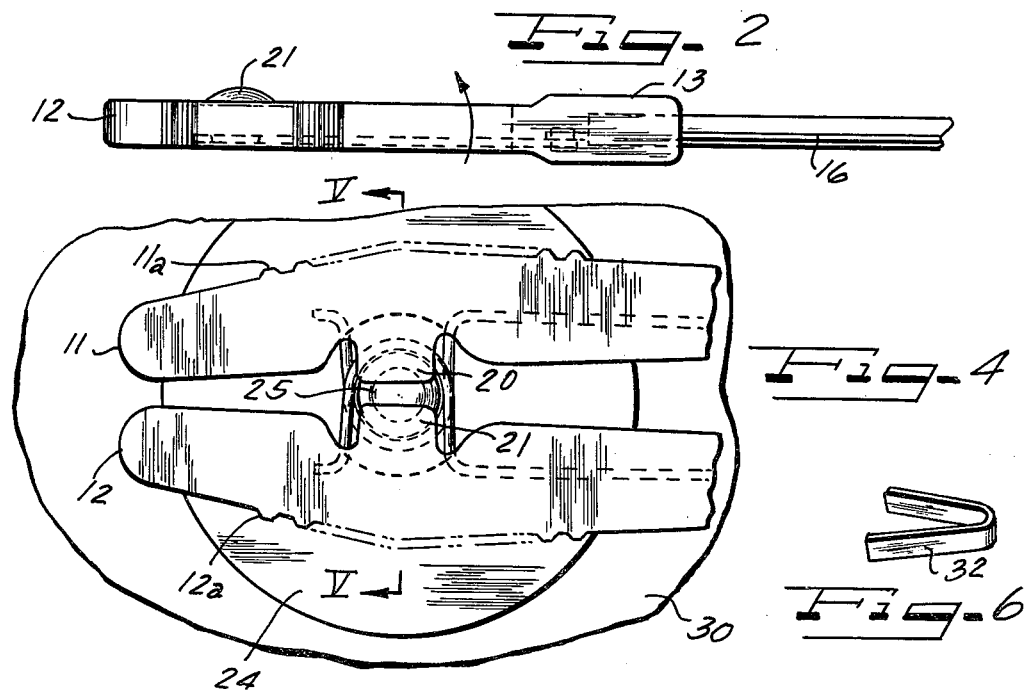
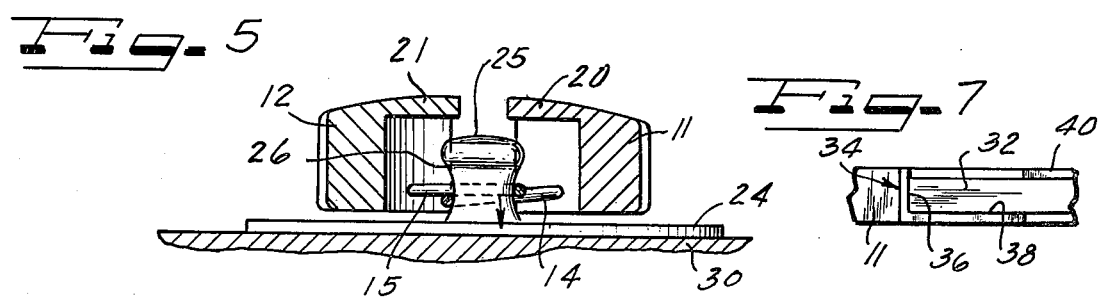

MEDICAL CLIP

BACKGROUND OF THE INVENTION

The present invention is related to a resilient clip for electrically connecting an electrical conductor cable associated with medical equipment or the like to a conventional male electrode. Such electrodes are well known in the medical field and typically comprise a conductive male projection having an enlarged head for association with the clip and a base carried by a patch or the like adhesively secured to the patient. Such an electrode is shown, for example, in U.S. Pat. No. 3,750,094 dated July 31, 1973, and another similar structure is shown in U.S. Pat. No. 3,606,881 dated Sept. 21, 1971. This male-type electrode is typically called the "snap-on" or "button" type of terminal.

To such conventional male-type electrodes, the prior art has applied snap-on terminals and terminals comprising a pair of pivotal plates normally biased apart but movable into overlapping condition to provide passage of the enlarged portion of the male electrode. Upon subsequent release of a closing force, the plates have operated to tend to retain the clip in position on the male projection, below the enlarged head thereof.

I have found, however, in the utilization of prior systems known to me, that proper insulation of the clip conductor elements has not been provided, with the result that possible electrical disturbances may occur in the monitoring circuitry through inadvertent contact with the male electrode or exposed conductors carried by the clip. Further, I have found that the clips employed in the prior art may be inadvertently tilted by the application of a lifting force to the terminal cable conductors in a manner permitting a cam action tending to permit the clip to snap over the enlarged portion of the electrode and become disconnected therefrom.

The present invention is, accordingly, directed to providing a more secure medical clip which protects the circuit with which it is used from inadvertent disturbances, which is particularly secure in its attachment, and which is not subject to disconnection by way of inadvertent tilting action.

BRIEF DESCRIPTION OF THE INVENTION

As above described, the medical clip of the present invention has solved the problems in the prior art systems. In accordance with the present invention, the clip is constructed of a dielectric resilient plastic material in a generally V or wishbone configuration in which the arms are integrally molded to each other at one end and diverge to a spaced relationship at the other ends. Resilient wire loops are provided on each of the arms at points spaced from the one end and generally facing each other in a condition to overlap when the arms are biased by an external force towards each other. A shelf or projection is provided on at least one of the arms in a manner acting to cover the male electrode when the loops are overlapped and placed thereover. In accordance with the present invention, at least one of the arms is provided with an extension projecting substantially beyond the location of the wire loop such that any tendency of the clip to tilt about the male electrode will be prevented by impingement of the extension upon the base of the male electrode. Pivotal motion of the clip 360 degrees around the male projection is, of course, maintained.

It has been found that the resiliency of the overlapping loops provides a flexibility therein resisting the inadvertent removal of the clip from the male electrode by pulling the clip in a direction longitudinally of the male electrode without pressing the arms of the clip together. Accordingly, in accordance with the present invention, a medical clip having superior retentivity and electrical insulation characteristics has been provided.

BRIEF DESCRIPTION OF THE DRAWINGS

FIG. 1 is a plan view of a clip constructed in accordance with the present invention;

FIG. 2 is a side-elevational view of the clip shown in FIG. 1;

FIG. 3 is a plan view of a modified clip shown in FIG. 1;

FIG. 4 is an enlarged partial plan view of the clip shown in overlapped relation in the position of application onto a snap-on male electrode;

FIG. 5 is a cross-sectional view taken along the line V—V of FIG. 4, with the clip in its final released condition on the male electrode; and FIGS. 6 and 7 illustrate a spring and a fragmentary view of a spring retention means on one arm of a clip as a further feature of the clip shown in FIG. 1.

As can be seen from a consideration of FIGS. 1 and 2, the medical clip, generally indicated at 10, is preferably formed of a plastic body comprised of arms 11 and 12 integrally molded to end portion 13. The V or wishbone shape of the clip as viewed in FIG. 1, comprises the "at rest" or normal condition of the clip. Wire loops 14, 15 of conductive material are embedded in the respective arms 11, 12 and extend, embedded therein, longitudinally of the respective arms, to separate connection with the conductors 17, 16. Typically, the clip 10 may be manufactured of a clear polycarbonate such as that marketed by General Electric Company under its trademark LEXAN®. Preferably, the polycarbonate is molded by the insert molding technique in which the wire loops 14, 15 and the conductors 17, 16 are positioned in the mold and the plastic molded thereabout to provide an integrated clip.

The clip 10 is intended for use with a conventional male electrode having an enlarged head 25 supported upon a projection having an inturned annular shoulder 26. The electrode 25 is typically connected to a conductive plate 24 which may be adhered to a patient, or other subject to be monitored, 30. The construction of the electrode 25 and its attachment to a subject is conventional and forms no part of the present invention.

Application of the clip to the male electrode may be understood from a consideration of FIGS. 4 and 5. As can be seen from FIG. 4, the arms 11 and 12 may be pressed toward each other manually into the position shown, in which the wire loops 14, 15 are in an overlapped condition in which the enlarged portion of the electrode 25 will pass therethrough. The position of the parts shown in FIG. 4 is the minimum condition of overlap in which the clip will pass over the electrode 25, and as can be observed, the arms 11, 12 may be pressed somewhat closer together, if desired, to facilitate the application of the clip to the electrode. When the clip passes completely over the enlarged portion 25 of the male electrode, it assumes the position shown in FIG. 5. As there shown, the arms 11, 12, have separated somewhat and are prevented from further separation by cooperation of the wire loops 14, 15, with the neck of the male electrode. As can be seen, shelves, or projections, 20,21 are carried by the respective arms, 11,12, and cover the electrodes 25 in a substantial manner. As a result of this relationship, inadvertent touching of the electrode 25 by the patient or by a medical attendant, is avoided.

Preferably, the wire loops 14, 15 are constructed of a spring wire having resiliency which will permit deflection of the wire loops in the direction of the arrow shown in FIG. 5 when the arms 11, 12 are moved upwardly away from the plate 24. This deflection or pivotal action of the loops about their points of support in the arms 11, 12 cooperates with the curved shoulder 26 to snugly grip the electrode tightly, resisting any tendency of the wire loops to slide upwardly along the electrode in a manner that would permit disassembly of the clip from the electrode.

As pointed out above, a tilting force may be applied to the clip in the direction of the arrow shown in FIG. 2. If the left-hand ends of the arms 11, 12 as viewed in FIGS. 1 and 4, were terminated immediately adjacent the electrode 25, such tilting motion could be carried to excess in a manner causing a camming action between the electrode 25 and the loops 14, 15. Such action would permit the arms 11, 12 to be forced toward each other, and the clip to slip off the electrode. In accordance with the structure of the present invention, the arms 11 and 12 extend substantially beyond the loops 14, 15 such that any tilting action is held to a minimum by contact of the extended ends with the plate 24 or the patient 30.

In the application of the clip to the electrode, the manual application of force to the arms 11, 12 is facilitated by the corrugated surfaces 11a, 12a. The possibility of slippage is thereby minimized. In the application of the clip to the electrode, the shelves or projections 20, 21 may act as abutments to indicate to the user that the loops 14, 15 are in a completely overlapped condition for application to the electrode. Clips of the type illustrated may be constructed in various sizes and materials. A very satisfactory clip has embodied an overall length of about two inches with an included angle of about 12 degrees between arms 11, 12, an arm extension beyond the electrode of about 0.45 inches, and a loop wire of about 0.015 inches.

In order to insure circuit isolation upon disengagement and not rely on the memory characteristic of the plastic material, a wishbone-shaped spring 32 may be provided (FIG. 6) and retained as illustrated in FIG. 7. The arm 11 is formed with an L-shaped inwardly extending projection 34 having a forward stop shoulder 36 and a bottom protective ledge 38 which prevents contact between the spring 32 and the electrode 25 and prevents downward movement of the spring. The arm 12 is similarly constructed. An inwardly projecting upper ledge 40 prevents upward movement of the spring 32. The ledge 40 extends around the common connection of the arms and similarly along the arm 12.

Modifications may, of course, be made to the embodiment illustrated without departing from the novel concepts of the present invention. For example, the loops 14, 15, may be directly connected to each other by way of a single conductive clip 19 shown in the modified form of FIG. 3. Similarly, the shelves or projections 20, 21 may be revised to provide a single shelf on one of the arms with a cooperative recess on the other. Similarly, the extending portion of one of the arms 11 or 12 may be eliminated, since only a single one of the arms need extend beyond the loops 14, 15 to prevent the tilting motion described above. It will, accordingly, be clear to those skilled in the art that the scope of the invention should be limited solely by that of the hereinafter appended claims.

I claim as my invention:

1. A terminal clip for use with electrodes of the general type having a male projection with an enlarged diameter head portion thereon, comprising a pair of support arms secured together at one end and normally spaced from each other at the other end, a resilient conductive wire loop extending from each of said arms at points spaced from said one end and overlappable with each other when the arms are moved toward each other to form an aligned aperture sufficiently large to pass said head portion when so overlapped, electrical conductor means connected to said wire loops, and means urging said arms apart to prevent the wire loops from being so overlapped unless external closing forces are applied to said arms, said support arms being integrally formed of resilient dielectric plastic with an initial unstressed generally V-shaped, at least one of said arms including a shalf carried thereby and projecting toward the other arm and transversely spaced from its respective wire loop to cover said head portion when said loops are so overlapped, said shelf cooperating with the arm toward which it projects providing an abutted condition signalling that the loops are so overlapped.

2. The terminal set forth in claim 1 wherein at least one of said arms extends substantially beyond its respective loop in the direction away from said one end to prevent tilting of said clip relative to the said electrode.

3. The terminal clip set forth in claim 1 wherein said wire loops resiliently deflect under said head portion to pivotably move about an axis generally parallel to said arms and spaced from the center of said head portion to accommodate movement of the clip away from said electrode without permitting disassembly therefrom.

4. The terminal clip set forth in claim 1, wherein the last-mentioned means comprises a spring coupled between said arms to decrease the recovery time upon disengagement from said electrode.

* * * * *